United States Patent
Fenton

(10) Patent No.: US 7,029,464 B2
(45) Date of Patent: Apr. 18, 2006

(54) OSTOMY POUCH WITH STRETCH-TO-FIT STOMA OPENING

(75) Inventor: Gary H. Fenton, Bedford, OH (US)

(73) Assignee: Marlen Manufacturing & Development Co., Beford, OH (US)

( * ) Notice: Subject to any disclaimer, the term of this patent is extended or adjusted under 35 U.S.C. 154(b) by 389 days.

(21) Appl. No.: 10/403,595

(22) Filed: Mar. 31, 2003

(65) Prior Publication Data

US 2004/0193123 A1    Sep. 30, 2004

(51) Int. Cl.
*A61F 5/44* (2006.01)

(52) U.S. Cl. .................. 604/338; 604/277; 604/336

(58) Field of Classification Search ............... 604/277, 604/327–355
See application file for complete search history.

(56) References Cited

U.S. PATENT DOCUMENTS

| | | | |
|---|---|---|---|
| 2,818,069 A | 12/1957 | Fenton | |
| 3,283,757 A | 11/1966 | Nelsen | |
| 3,295,145 A | 1/1967 | Ericson | |
| 4,387,713 A | 6/1983 | Calanni | |
| 4,561,858 A | 12/1985 | Allen, Jr. et al. | |
| 4,834,731 A | 5/1989 | Nowak et al. | |
| 4,973,323 A * | 11/1990 | Kaczmarek et al. | 604/338 |
| 5,000,748 A | 3/1991 | Fenton | |
| 5,004,464 A * | 4/1991 | Leise, Jr. | 604/338 |
| 5,015,244 A | 5/1991 | Cross | |
| 5,330,454 A | 7/1994 | Klingler et al. | |
| 5,429,626 A | 7/1995 | Fenton | |
| 5,607,413 A * | 3/1997 | Holmberg et al. | 604/342 |
| 5,730,735 A * | 3/1998 | Holmberg et al. | 604/338 |
| 6,673,056 B1 * | 1/2004 | Metz et al. | 604/338 |
| 6,790,200 B1 * | 9/2004 | Fenton | 604/338 |
| 6,840,924 B1 * | 1/2005 | Buglino et al. | 604/337 |
| 6,869,422 B1 * | 3/2005 | Fenton | 604/338 |

FOREIGN PATENT DOCUMENTS

EP    1 464 308 A1 * 10/2004

OTHER PUBLICATIONS

United Surgical Corporation, Expendable Drainage Bags, 1968.

* cited by examiner

*Primary Examiner*—Tatyana Zalukaeva
*Assistant Examiner*—Michael G. Bogart
(74) *Attorney, Agent, or Firm*—Pearne & Gordon LLP

(57) ABSTRACT

A ostomy device having a mounting disc and an ostomy pouch with a stoma receiving portal. The mounting disc is sealed about the portal and includes a flexible plastic disc having a convex central body portion and surrounding annular rim. A foam disc is adhesively adhered to the plastic disc, and a first skin barrier disc having an outer diameter corresponding to the outer diameter of the foam disc is adhesively adhered to an adhesive face of the foam disc. The skin barrier disc includes an inner diameter that is stretchable from a smallest diameter that is a point distal from an inner diameter of the plastic disc to a largest diameter that is substantially corresponding to an inner diameter of the plastic disc.

18 Claims, 3 Drawing Sheets

OSTOMY POUCH WITH STRETCH-TO-FIT STOMA OPENING

FIELD OF INVENTION

The present invention relates to ostomy assembly devices and, more particularly, to the mounting disc of an ostomy pouch.

BACKGROUND OF THE INVENTION

The present invention is an improvement of the ostomy assembly device of co-pending application, Ser. No. 09/758,726, incorporated herein by reference.

Ostomy assembly device generally have a mounting faceplate interposed between a convex disc and an ostomy pouch.

BRIEF SUMMARY OF THE INVENTION

This invention provides for a flexible skin barrier disc, which can be stretched to fit irregular stomas. According to one aspect the present invention, an ostomy device includes a mounting disc and an ostomy pouch with a stoma receiving portal. The mounting disc is sealed about the portal and includes a flexible plastic disc having a convex central body portion and surrounding annular rim. A foam disc is adhesively adhered to the plastic disc, and a first skin barrier disc having an outer diameter corresponding to the outer diameter of the foam disc is adhesively adhered to an adhesive face of the foam disc. A second skin barrier disc is adhesively adhered to the first skin barrier disc and has an inner diameter that is stretchable from a smallest diameter that is distal from an inner diameter of the plastic disc to a largest diameter that substantially corresponds to an inner diameter of the plastic disc.

According to a further aspect of this invention, an ostomy device includes a mounting disc and an ostomy pouch with a stoma receiving portal. The mounting disc is sealed about the portal and includes a flexible plastic disc having an annular rim. A first foam disc is adhered to the plastic disc and has an outer diameter substantially corresponding to the outer diameter of the flexible plastic disc. A second foam disc is adhered to the first foam disc and has an outer diameter greater than the outer diameter of the flexible plastic disc. An adhesive skin barrier disc is adhered to the second foam disc and has an outer diameter substantially corresponding to the outer diameter of the second foam disc. The skin barrier disc has an inner diameter that is stretchable from a smallest diameter that is distal from an inner diameter of the plastic disc to a largest diameter that substantially corresponds to an inner diameter of the plastic disc.

DETAILED DESCRIPTION OF THE INVENTION

Figure 1:
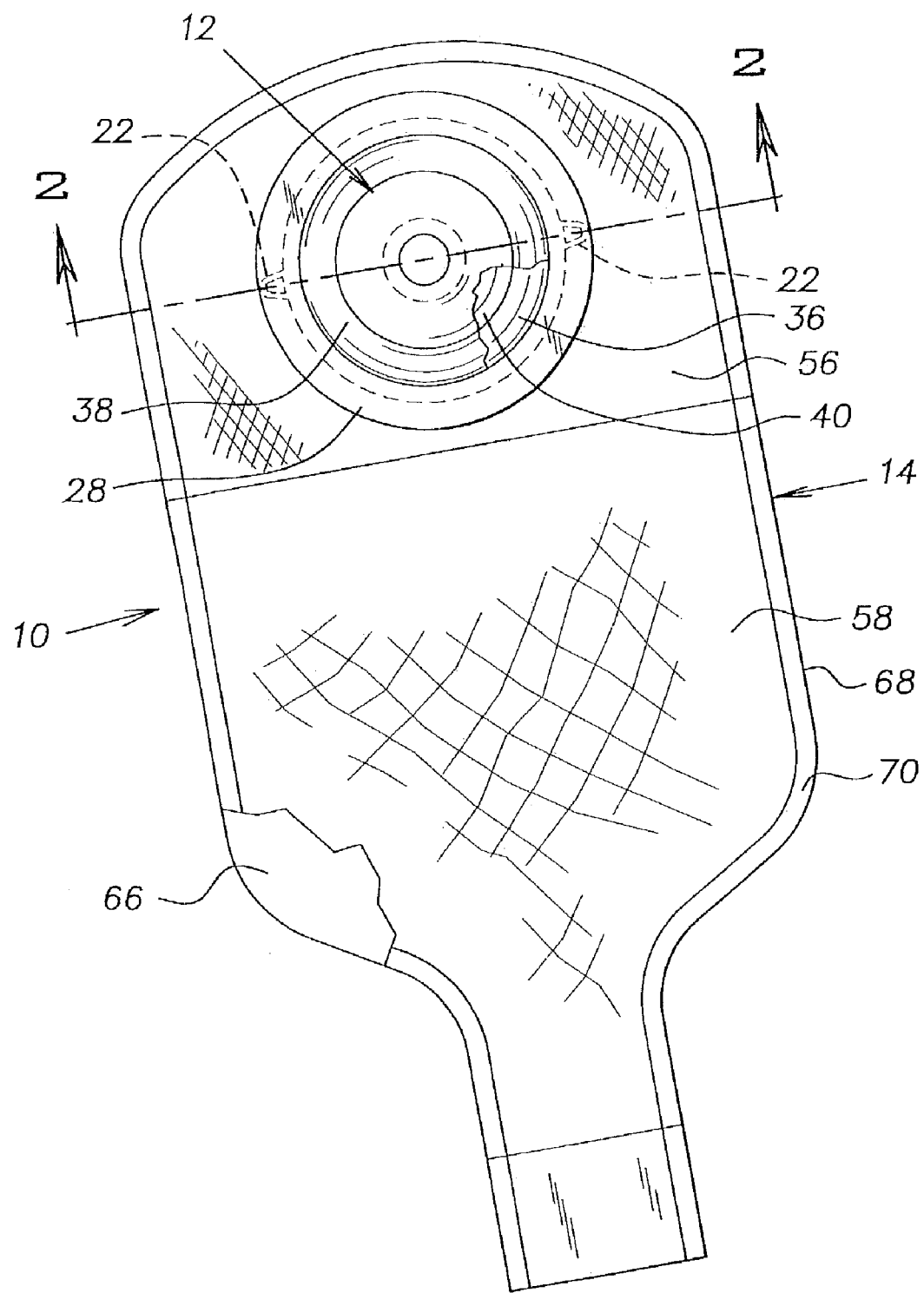
FIG. 1 is a proximal elevational view of an ostomy device according to one aspect of the present invention.
Figure 2:
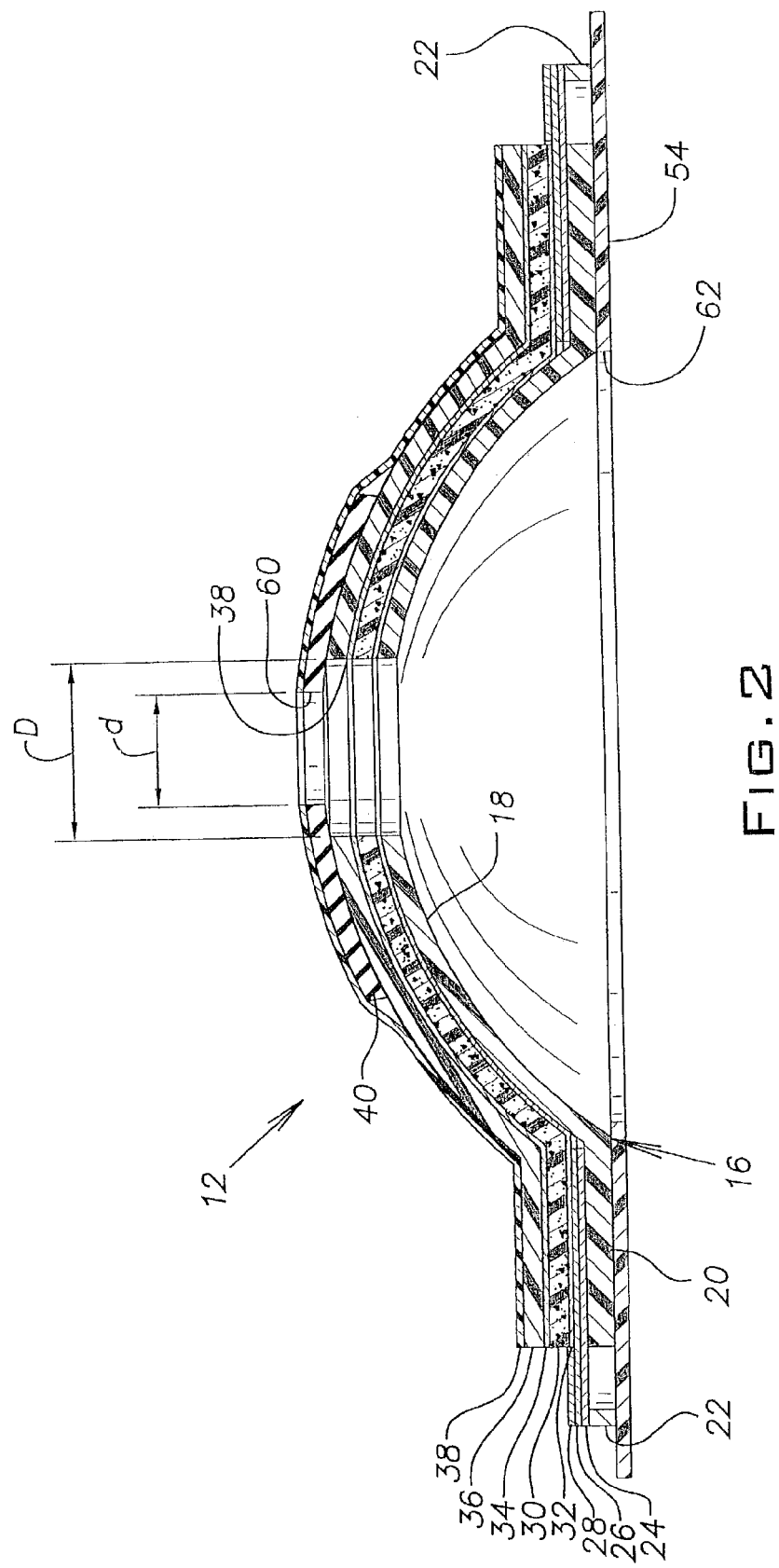
FIG. 2 is a cross-sectional view, the plane of the section being indicated by the line 2—2 in FIG. 1.

Referring now to FIGS. 1 and 2 of the drawings, there is illustrated an ostomy device assembly 10 according to this invention. The assembly 10 includes a mounting disc 12 and an ostomy pouch 14.

The mounting disc 12 includes a flexible plastic disc 16 having a convex central body portion 18 and surrounding annular rim 20. The disc 16 is provided with diametrically opposed and radially extending belt mounting loops 22 at its periphery for a fastening belt (not shown).

A cloth-like porous material disc 24 covers the flexible plastic disc 16. The cloth-like disc has an adhesive layer 26 on one face, and the other face of the cloth-like disc is adhesively attached to the surrounding annular rim 20 of the plastic disc 16. The cloth-like disc, when applied to the disc 16, has an inner diameter that is substantially the same as the outer diameter of the convex central body portion 18 of the plastic disc 16. The cloth-like disc 24 has an outer diameter that is greater than the outer diameter of the plastic disc 16 and that substantially extends over mounting loops 22 so that the skin of the ostomate is protected from belt hooks (not shown) passing through the loops 22. Preferably, the exposed surface of the cloth-like disc 24 is covered by a thin release paper 28, which is removed just prior to use.

A soft, resilient thermoplastic foam disc 30 covers the cloth-like disc 24. The foam disc 30 has pressure-sensitive adhesive layers 32 and 34 on each of its faces and one face is attached to the cloth-like disc 24 and convex portion 18 of the plastic disc 16. The foam disc 30, when applied to the cloth-like disc 24, has an outer diameter that is greater than the outer diameter of the convex central body portion 18 of the plastic disc 16.

A first adhesive hydrocolloid skin barrier disc 36 having an inner and outer diameter corresponding to that of the foam disc 30 is placed on the adhesive layer 32 of the foam disc 30. Preferably, the exposed surface of the first skin barrier disc 36 is covered by a thin release film 38 which is removed just prior to use. The first skin barrier disc 36 is pliable and has both dry and wet tack.

A second adhesive hydrocolloid skin barrier disc 40 is placed on the first skin barrier disc 36. Preferably, the exposed surface of the second skin barrier disc 40 is covered by the thin release film 38 which is removed just prior to use. The second skin barrier disc 40 is pliable and has both dry and wet tack. The second skin barrier disc 40 has an opening 60 having inner diameter d that is stretchable from a smallest diameter of about ½ inch to a largest inner diameter D of about 2 inches that substantially corresponds to the inner diameter of the plastic disc 16.

The stretchability of the opening 60 is to any diameter between about ½ inch and 2 inches and to any irregular shape within the stretchable zone. This aspect of the invention permits the user to stretch the opening 60 to fit the size and/or shape of the users stoma without cutting the opening with scissors.

Figure 3:
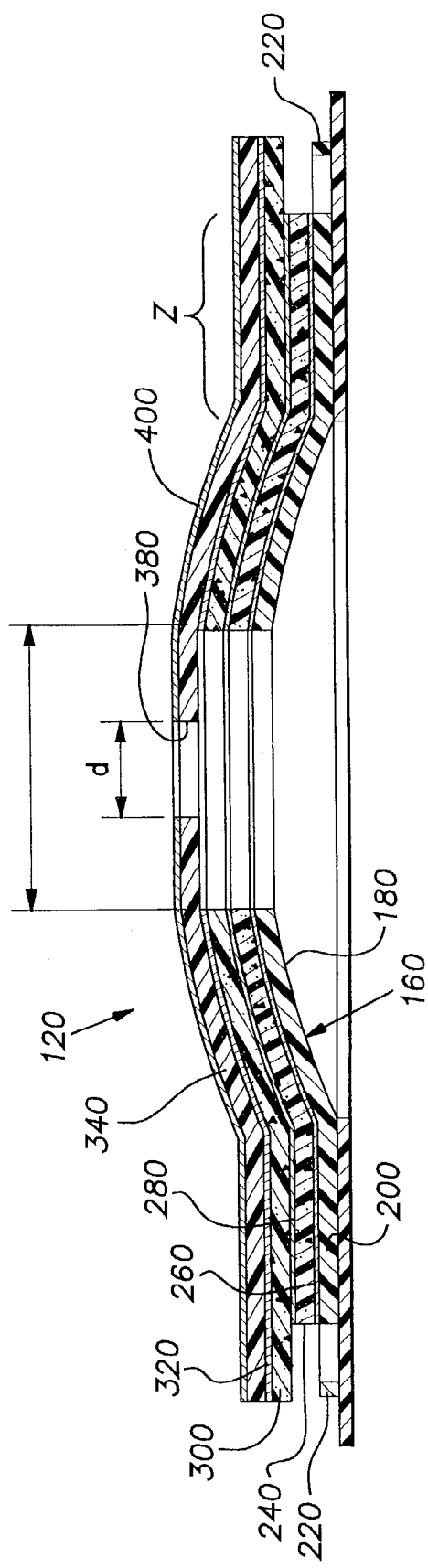
FIG. 3 is a cross-sectional view, similar to FIG. 2 but illustrating an ostomy device according to a further aspect of the invention.

Referring now to FIG. 3 of the drawings, there is illustrated an ostomy appliance assembly according to another aspect of this invention. The assembly includes a mounting disc 120, adapted to be attached to a fastening belt (not shown) of an ostomate, and an ostomy pouch (not shown in this view).

The mounting disc 120 includes a flexible plastic disc 160 having a convex central body portion 180 and a surrounding annular rim 200. The disc 160 is provided with diametrically opposed and radially extending belt mounting loops 220 at is periphery.

A first soft resilient thermoplastic foam disc 240 covers the flexible plastic disc 160. The foam disc 240 has pressure-sensitive adhesive layers 260 and 280 on each of its faces and one face is attached to the plastic disc 160. The foam disc 240, when applied to the disc 160, has an outer diameter substantially corresponding to the outer diameter of the disc 160.

A second soft, resilient thermoplastic foam disc 300 covers the first foam disc 240. The second foam disc 300 has a pressure-sensitive adhesive layer 320 on one face, and the other face of the disc 240 is adhesively attached to the adhesive layer 280 of the first foam disc 240 so that the pressure-sensitive layer is exposed. The second foam disc 300 has an outer diameter greater than the outer diameters of the first foam disc 240 and the plastic disc 160. The mating loops 220 do not extend beyond the diameter of the second foam disc 300 so that the skin of the ostomate is protected from belt hooks passing through the loops 220.

An adhesive hydrocolloid skin barrier disc 340 having an outer diameter corresponding to that of the second foam disc 300 is placed on the adhesive layer 320 of the second foam disc 300. Preferably the exposed surface of the disc 340 is covered by a thin release film 400 which is removed just prior to use. Heat and pressure are applied to an annular zone z to seal the discs and to smooth the foam and hydrocolloid discs over the convex central body portion 180 of the plastic disc 160.

The adhesive skin barrier disc 340 is pliable and has both dry and wet tack. Suitable materials are Karaya-glycerine formulations or mixtures of polyacrylamide resins and other polyols and mixtures of elastomers and hydrocolloids. A stoma inlet portal 380 is provided at the center of the assembly.

The exposed surface of the skin barrier disc 340 is covered by the thin release film 400 which is removed just prior to use.

The opening 380 in the skin barrier disc 340 has an inner diameter d that is stretchable from a smallest diameter of about ½ inch to a largest diameter D of about 2 inches that substantially corresponds to the inner diameter of the plastic disc 160.

The stretchability of the opening 380 is to any diameter between about ½ inch to 2 inches and to any irregular shape within the stretchable zone. This aspect of the invention permits the user to stretch the opening 380 to fit the size and/or shape of the users stoma without cutting the opening with scissors.

While the invention has been shown and described with reference to a specific embodiment, various changes may be made and equivalents may be substituted for elements thereof by those skilled in the art without departing from the scope of the invention. In addition, other modifications may be made to adapt a particular situation or material to the teachings of the invention without departing from the essential scope thereof. Accordingly, the invention is not to be limited in scope and effect to the specific embodiment herein described, nor in any other way that is inconsistent with the extent to which the progress in the art has been advanced by the invention, except insofar as indicated in the appended claims.

What is claimed is:

1. A mounting disc for an ostomy pouch comprising:
   a flexible plastic disc having a convex central body portion and a surrounding annular rim;
   a foam disc having first and second faces and having pressure-sensitive adhesive on each of said faces, the second face of said foam disc being adhered to the convex central body portion and the surrounding annular rim of the plastic disc;
   a first adhesive skin barrier disc having an outer diameter substantially corresponding to the outer diameter of said foam disc, said first skin barrier disc being adhered to the first face of said foam disc; and
   a second adhesive skin barrier disc being adhered to the first face of said first skin barrier disc, said second skin barrier disc having an inner diameter that is stretchable from a smallest diameter that is a point distal from an inner diameter of said plastic disc to a largest diameter that is substantially corresponding to the inner diameter of said plastic disc.

2. A mounting disc as in claim 1 including diametrically opposed and radially extending mounting loops at a periphery of said flexible plastic disc.

3. A mounting disc as in claim 1 including a cloth-like disc having first and second faces and having adhesive on said first face, said cloth-like disc having an outer diameter greater than an outer diameter of said flexible plastic disc, the second face of said cloth-like disc being adhered to the surrounding annular rim of the plastic disc and the first face of said cloth-like disc being adhered to the foam disc.

4. A mounting disc as in claim 3, wherein said mounting loops do not substantially extend beyond the diameter of the cloth-like disc.

5. A mounting disc as in claim 1, including a removable protective film covering the first face of said second skin barrier disc.

6. A mounting disc for an ostomy pouch comprising:
   a flexible plastic disc having a convex central body portion and a surrounding annular rim;
   a cloth-like disc having first and second faces and having pressure-sensitive adhesive on said first face, said cloth-like disc having an outer diameter greater than an outer diameter of said flexible plastic disc, the second face of said cloth-like disc being adhered to the surrounding annular rim of the plastic disc;
   a foam disc having first and second faces and having pressure-sensitive adhesive on each of said faces, the second face of said foam disc being adhered to the cloth-like disc and the convex central body portion of the plastic disc;
   a first adhesive skin barrier disc having an outer diameter substantially corresponding to the outer diameter of said foam disc, said first skin barrier disc being adhered to the first face of said foam disc; and
   a second adhesive skin barrier disc being adhered to the first face of said first skin barrier disc, said second skin barrier disc having an inner diameter that is stretchable from a smallest diameter that is a point distal from an inner diameter of said plastic disc to a largest diameter that substantially corresponds to the inner diameter of said plastic disc.

7. A mounting disc as in claim 1, including a removable protective film covering the first face of said second skin barrier disc and a removable protective paper covering the first face of said cloth-like disc.

8. A mounting disc as in claim 7 including diametrically opposed and radially extending mounting loops at a periphery of said flexible plastic disc, said mounting loops do not substantially extend beyond the diameter of the cloth-like disc.

9. A ostomy device comprising:
a mounting disc and an ostomy pouch;
said mounting disc comprising a flexible plastic disc having a convex central body portion and a surrounding annular rim,
a foam disc having first and second faces and having pressure-sensitive adhesive on each of said faces, the second face of said foam disc being adhered to the convex central body portion and the surrounding annular rim of the plastic disc,
a first adhesive skin barrier disc having an outer diameter substantially corresponding to the outer diameter of said foam disc, said first skin barrier disc being adhered to the first face of said foam disc, and
a second adhesive skin barrier disc being adhered to the first face of said first skin barrier disc, said second skin barrier disc having an inner diameter that is stretchable from a smallest diameter that is a point distal from an inner diameter of said plastic disc to a largest diameter that is substantially corresponding to the inner diameter of said plastic disc; and
said ostomy pouch comprising proximal and distal sheets of plastic film sealed at their peripheries, said proximal sheet having a stoma inlet portal therein, said inlet portal having a diameter substantially corresponding to an inside diameter of the annular rim of said flexible plastic disc, said annular rim being sealed to said proximal sheet about a zone surrounding said portal.

10. A mounting disc as in claim 9 including diametrically opposed and radially extending mounting loops at a periphery of said flexible plastic disc.

11. A mounting disc as in claim 10 including a cloth-like disc having first and second faces and having adhesive on said first face, said cloth-like disc having an outer diameter greater than an outer diameter of said flexible plastic disc, the second face of said cloth-like disc being adhered to the surrounding annular rim of the plastic disc and the first face of said cloth-like disc being adhered to the foam disc.

12. A mounting disc as in claim 11, wherein said mounting loops do not substantially extend beyond the diameter of the cloth-like disc.

13. A mounting disc as in claim 9, including a removable protective film covering an exposed first face of said first skin barrier disc and the first face of said second skin barrier disc.

14. A mounting disc for an ostomy pouch comprising a flexible plastic disc having a convex central body portion and a surrounding annular rim, a first foam disc having first and second faces and having pressure-sensitive adhesive on each of said faces, said first foam disc having an outer diameter substantially corresponding to the outer diameter of said flexible plastic disc, the second face of said first foam disc being adhered to the convex central body portion and the surrounding annular rim of the plastic disc, a second foam disc having first and second faces and having pressure-sensitive adhesive on said first face of said second foam disc, said second foam disc having an outer diameter greater than the outer diameter of said flexible plastic disc, the second face of said second foam disc being adhered to the first face of said first disc, an adhesive skin barrier disc having an outer diameter substantially corresponding to the outer diameter of said second foam disc, said skin barrier disc being adhered to the first face of said second foam disc, said skin barrier disc having an inner diameter that is stretchable from a smallest diameter that is a point distal from an inner diameter of said plastic disc to diameter that substantially corresponds to the inner diameter of said plastic disc.

15. A mounting disc according to claim 14 including diametrically opposed and radially extending mounting loops at a periphery of said flexible plastic disc.

16. A mounting disc according to claim 15 wherein said mounting loops do not extend beyond the diameter of the skin barrier disc and the second foam disc.

17. A mounting disc according to claim 14 wherein the skin barrier disc is an elastomer hydrocolloid mixture.

18. A mounting disc according to claim 14 including a removable protective film covering another face of said skin barrier disc.

* * * * *